United States Patent [19]
Daggett

[11] Patent Number: 5,217,890
[45] Date of Patent: Jun. 8, 1993

[54] STABILIZED COMPOSITION CONTAINING CREATINE KINASE AND PROTEIN HAVING BLOCKED SULFHYDRYL GROUPS

[75] Inventor: Stephen G. Daggett, Rochester, N.Y.

[73] Assignee: Eastman Kodak Company, Rochester, N.Y.

[21] Appl. No.: 747,780

[22] Filed: Aug. 20, 1991

[51] Int. Cl.⁵ .......................... C12N 9/96; C12N 9/12
[52] U.S. Cl. ..................................... 435/188; 435/194
[58] Field of Search ................................ 435/188, 194

[56] References Cited

U.S. PATENT DOCUMENTS

| | | | |
|---|---|---|---|
| 3,876,375 | 4/1975 | Maurukas | 435/188 |
| 4,229,369 | 10/1980 | Green | 435/188 |
| 4,276,376 | 6/1981 | Hundt et al. | 435/188 |
| 4,652,524 | 3/1987 | Modrovich et al. | 435/188 |
| 4,684,615 | 8/1987 | Hoskins | 436/16 |
| 4,931,392 | 6/1990 | Rehner et al. | 435/188 |

FOREIGN PATENT DOCUMENTS

| | | | |
|---|---|---|---|
| 57-122796 | 7/1982 | Japan | 435/188 |
| 58-162294 | 9/1983 | Japan | 435/188 |
| 340693 | 6/1972 | U.S.S.R. | 435/188 |

OTHER PUBLICATIONS

Terrence A. Cooper, "The Tools of Biochemistry", (1977), pp. 365–367.
Means and Feeney, Chemical Modification of Proteins, Holden and Day, Inc., (1977), pp. 149–173.

Primary Examiner—David M. Naff
Assistant Examiner—Michael Meller
Attorney, Agent, or Firm—Doreen M. Wells

[57] ABSTRACT

A method of stabilizing creatine kinase in a protein solution is disclosed. Sulfhydryl groups in the protein solution are modified and rendered unreactive with creatine kinase. The sulfhydryl groups are blocked with a blocking agent such as cystine.

10 Claims, 2 Drawing Sheets

STABILIZED COMPOSITION CONTAINING CREATINE KINASE AND PROTEIN HAVING BLOCKED SULFHYDRYL GROUPS

FIELD OF THE INVENTION

The present invention relates generally to clinical chemistry. In particular, it relates to a process for stabilizing creatine kinase activity.

BACKGROUND OF THE INVENTION

The determination of the activity of creatine kinase (abbreviated herein to CK, but also known as creatine phosphokinase, and CPK) is useful in the diagnosis of diseases such as progressive muscular dystrophy, dermatomyositis, and myocardial infarctions. CK occurs in human body fluids and tissue in the form of different isoenzymes: for example, CK-MM in muscles, CK-BB in the brain, and CK-MB in the myocardium. The CK activity occurring in healthy human blood serum is normally due to the CK-MM isoenzyme, because CK-BB does not generally pass into the blood stream. In a healthy individual, the CK-MB is generally restricted to certain organs, e.g. the myocardium. However, when the myocardium is damaged, as in the case of a cardiac infarction, CK-MB is released into the blood serum and can be detected therein.

Clinical devices which determine the amount of CK or CK-MB in serum require calibration as well as frequent quality control to indicate whether the diagnostic device is in proper operation. Compositions used for such quality control or calibration (hereafter control compositions) contain a known activity of the enzyme to be assayed. It is axiomatic that the enzyme activity of such controls not change substantially over time. Further, it is important that the enzyme present in the control composition behave in the same way as the enzyme present in the patient sample.

Some attempts to protect enzymes such as creatine kinase against loss of activity focus primarily on modifying the enzyme itself in some way. U.S. Pat. No. 4,931,392, for example, teaches, a two-step method comprising (a) disulfide modification of the enzyme, and (b) covalently binding an activated carbohydrate to creatine kinase.

The problem with this approach is that the control enzyme is altered and is therefore different from the native enzyme found in human sera. In this altered form, the enzyme might not behave or react like the native physiologically active enzyme and therefore might not be predictive of the enzyme activity in the patient sample. Such differences could lead to inaccurate results. Further, such altered enzymes are not commerically available and their preparation would increase the overall cost of the assay.

SUMMARY OF THE INVENTION

Figure 1:
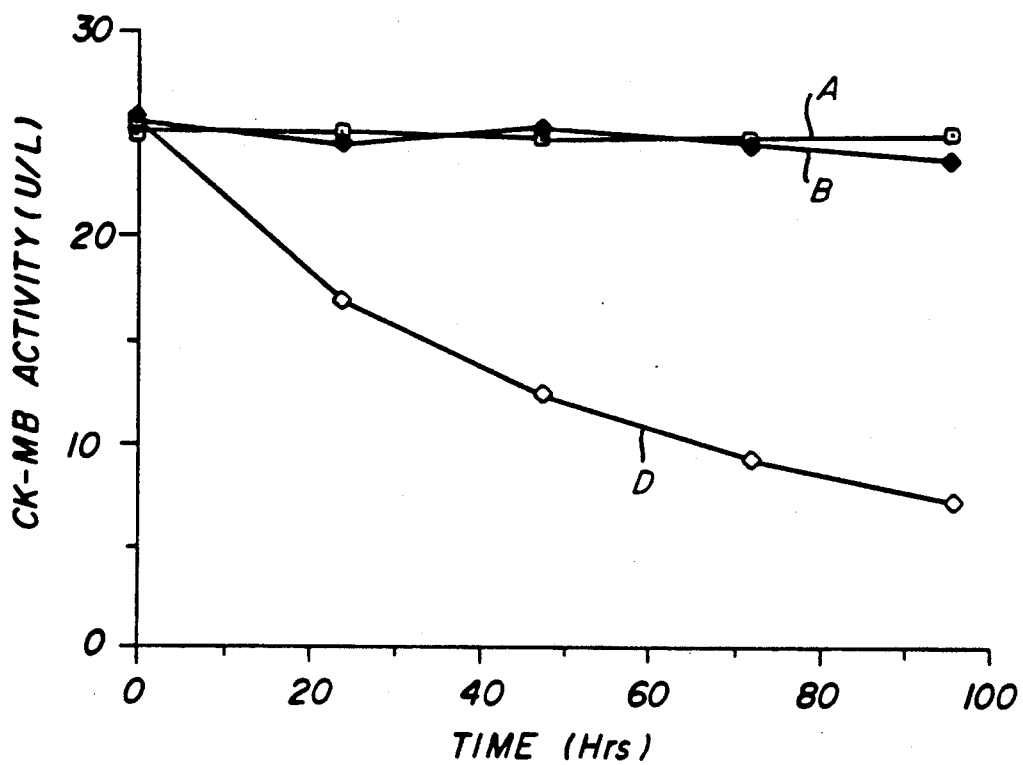
FIG. 1 is a graph showing CK-MB activity over time for two of compositions of the invention; one refrigerated, the other kept at room temperature.

The present invention overcomes the abovementioned problem by providing a composition comprising an enzyme having sulfhydryl groups in a reduced state in a protein having unreactive sulfhydryl groups.

The present invention also provides a method of stabilizing the activity of an enzyme comprising the steps of (a) preparing a solution of protein in water, wherein the protein has sulfhydryl groups that are unreactive, and (b) adding the enzyme to the solution.

In another aspect, the present invention also provides a method of calibrating a device for determining the activity of an enzyme, wherein one of the compositions of claim 1 or 2 is used as the calibrating composition.

We are aware of no prior art that teaches stabilization of enzyme activity in a solution with a protein having unreactive sulfhydryl groups. Prior art methods attempt to modify the enzyme itself. During the course of our research, we unexpectedly found that enzyme activity varies depending on the reactivity of the sulfhydryl groups of the protein used in the solution.

DETAILS OF THE INVENTION

As used herein, the term "control composition" generally describes an aqueous or lyophilized composition with a known enzyme activity. It is used to check the accuracy of a method, analytical element or instrument for testing enzyme activity. The control composition may be used as a specimen with known enzyme activity, or it may be used to calibrate the instrument.

The term "reactive sulfhydryl groups" refers to free sulfhydryl groups on a protein that can react with sulfhydryl groups on the enzyme. The term "unreactive sulfhydryl groups" refers to a protein substantially free of reactive sulfhydryl groups.

The term "sulfhydryl modified" means that the sulfhydryl groups on a protein have been blocked (also described in the art as "protected"), and thereby made unreactive with sulfhydryl groups on an enzyme.

An important mechanism affecting the stability of enzyme activity is oxidation of the free sulfhydryl groups on the enzyme and the resulting formation of disulfides. When these sulfhydryls are in a reduced state the enzyme is active; in an oxidized state, the enzyme is inactive.

Most proteins commonly encountered contain free sulfhydryl groups. One or more of these sulfhydryl groups can react with other free sulfhydryl groups and become oxidized. Oxidation usually results in loss of enzyme activity.

We postulated that if an enzyme having reactive sulfhydryls is carried in a reactive protein solution, reaction between the sulfhydryl groups on the protein and those on the enzyme could oxidize the sulfhydryl groups on the enzyme. Thus, elimination of free sulfhydryls from the protein would decrease enzyme inactivation rates.

Sulfhydryl groups can be made unreactive with many reagents. In the example of the invention given below, a commerically available preparation of BSA with blocked sulfhydryl groups was used. Useful reagents for blocking sulfhydryl groups include iodoacetate, N,ethylmaleimide, 5,5'-dithiobis (2-nitrobenzoic acid) (DTNB) (Ellman's Reagent), p-mercuribenzoate, 2-mercaptoethanol, cystine, reduced gluthathione, and thioglycolate. Procedures for the use of these reagents are disclosed in "The Tools of Biochemistry", Terrence A. Cooper, (1977) and in Means and Feeney, *Chemical Modification of Proteins* Holden and Day, Inc., (1977), but any procedure would be useful as long as the sulfhydryl groups in the protein solution are maintained in the reduced state and do not interact with the free sulfhydryl groups on an enzyme. It is important that any excess of the blocking reagent (that is, blocking reagent not blocking a sulfhydryl group) be removed so as not to react with the enzyme.

Various preparations of unreactive protein (meaning that the sulfhydryl groups are blocked) are commercially available. Compositions of the invention are made up in protein substances having sulfhydryl groups that have been made unreactive. Such proteins are selected from animal serum and serum albumin such as bovine serum albumin (BSA). BSA is preferred because it is a better defined, more consistent material in that there are various preparations that are commercially available and these have been purified, analyzed and described in detail by the manufacturers. Results are reproducible when such materials are used.

For the composition of the present invention, we used a sulfhydryl modified grade of BSA (Miles, Inc.) that was tested in our laboratory and confirmed to have significantly less free sulfhydryl groups than the unmodified grades.

The enzyme composition of the invention can be stored not only in liquid form at 4° C. to 25° C. but also in lyophilized form at any temperature up to 25° C. Using prior art methods, enzyme (e.g. CK) compositions reconstituted from the lyophilized form remain stable at refrigerated temperatures only for periods of hours. Unexpectedly, enzyme compositions prepared according to the method of the invention remain stable at room temperature for periods of up to 7 days and for 14 days when refrigerated. Other compositions not prepared in a sulfhydryl-modified protein solution begin to decline steadily in enzyme activity almost as soon as they are left at room temperature.

This invention improves the reproducibility and accuracy of enzyme assays and lowers the cost of performing such assays because unstable enzymatic solutions need not be as frequently discarded and replaced with fresh formulations.

EXAMPLES

Materials

CK-MB was obtained from Scripps, Catalog #C1223, San Diego, CA 92131. CK-MB from Scripps is stabilized in 50% glycerol, 5 mM succinate 10 mM sodium chloride, 2 mM B-mercaptoethanol, 1 mM EDTA at a pH of about 7.0. It is recommended that the preparation be stored at −20° C. and protected from light during storage.

The protein solution of the examples described herein comprises sulfhydryl modified BSA available from Miles, Inc., Kankakee, Il 60901. Miles' product catalog states that the free sulfhydryl groups on the sulfhydryl modified grade of BSA are blocked with L-cystine and tests conducted in our laboratory have confirmed that this BSA grade has little or no free sulfhydryls.

Magnesium Acetate, 1,4-piperazinebis(ethanesulfonic acid) (PIPES) buffer, tris(hydroxymethyl)aminomethane (TRIS) buffer, and Ethylenediaminetetraacetic acid (EDTA) are all commercial grade. Dry analytical elements for assaying total CK, or the CK-MB subunit of CK, were obtained from Eastman Kodak Company, Clinical Products Division, Rochester, NY 14650. 5,5'-Dithiobis(2-nitrobenzoic acid) (DTNB) was also obtained from Kodak.

EXAMPLE 1

A composition of CK-MB in Sulfhydryl Modified unreactive BSA

To manufacture the composition of the invention, the protein solution is first prepared. The protein solution contains all constituents of the composition except the selected enzyme. The volume of stock solution should be produced in quantities about 10% greater than the final volume needed. The extra protein solution is used to adjust the final composition to the required enzyme concentration.

The protein solution is prepared by adding 7.56 g of 1,4-piperazinebis(ethanesulfonic acid) (PIPES buffer) (25 mM, Sigma P-6757, MW=302.4); 0.6434 g Magnesium Acetate (3 mM, MW=214.46); 0.3722 g EDTA, (1 mM, MW=372.23); and 30 g Bovine Serum Albumin (Miles' sulfhydryl modified grade) to 500 mL of distilled deionized water (hereafter water) and stirring until all constituents are dissolved. Approximately 100 mL water is added and stirring continued for a few minutes. Sixty mg chloramphenicol (Sigma, C-0378); 25 mg gentamycin sulfate (U.S. Biochemical Corp., Catalog #16051 CAS 1405-41-0); and 1.50 g methyl paraben (methyl p-hydroxybenzoate, Kodak) are added and the mixture again stirred until all constituents are dissolved. The solution is adjusted with 10N NaOH to a pH of about 7.0 to 8.5 and refrigerated overnight at 25° C. The solution is then transferred to a 1-liter volumetric flask, and water added to a volume of 1 liter. The flask is inverted to mix the protein solution.

Other molar concentrations of PIPES buffer are also useful as are other buffers, provided that the final pH of the composition is about 7.0–8.5 and the buffer does not adversely interact with the other constituents of the composition. Other magnesium salts such as magnesium chloride may also be used. Ethylene glycol bis(B-aminoethyl ether) (EGTA) or other metal chelators may be used in place of EDTA. Any suitable protein with unreactive sulfhydryl groups may also be used. Also, other antibiotics or inhibitors of bacterial growth may be used in place of chloramphenicol, gentamycin and methyl paraben to protect the protein solution against growth of micro-organisms.

The final composition is made by adding sufficient CK-MB to the protein solution to provide a CK-MB activity of between 1 and 500 U/L in the composition. The total protein in the composition is about 0.3 to about 10.0 g/dL, but preferably about 0.7 to about 5.0 g/dL.

For further testing, the composition described above (at pH 7.5 with 3 g/dL sulfhydryl modified BSA,) was divided in two portions; one half was refrigerated, the other half was kept at room temperature for further experimentation, described below.

A. Composition of CK-MB stored at refrigerator temperature

The portion of the composition described above in Example 1 as refrigerated (at 4° C.) was designated sample A and assayed for CK-MB activity over a period of 100 hours. Ten uL of sample A was spotted on a Kodak Ektachem ™ analytical element for assaying CK-MB. CK-MB activity was determined on the Ektachem ™ automatic analyzer. The results are shown in FIG. 1.

B. Composition of CK-MB stored at room temperature

The portion of the composition described in Example 1 as set aside (designated Sample B) was stored at room temperature so as to exert thermal stressing, as is customary in the art when performing stability tests. Sample D represents a prior art CK composition prepared in a protein solution of reactive human serum 5.3 g/dL at pH 7.0 and includes: a reducing agent, B-thio-D-glucose (3 mM); CK-MB from human heart; and CK-MM as found in human serum. Samples B and D were assayed for CK-MB activity in the same manner as sample A.

The results, also shown in FIG. 1, demonstrate that the composition of the invention maintains CK-MB activity for up to about 96 hours whether refrigerated or unrefrigerated. Even after remaining unrefrigerated for about 96 hours, the unrefrigerated sample demonstrates substantial CK-MB activity. The enzyme activity in Sample D declined steadily from time 0.

C. CK-MB Stability with Increasing Unreactive BSA

Figure 2:
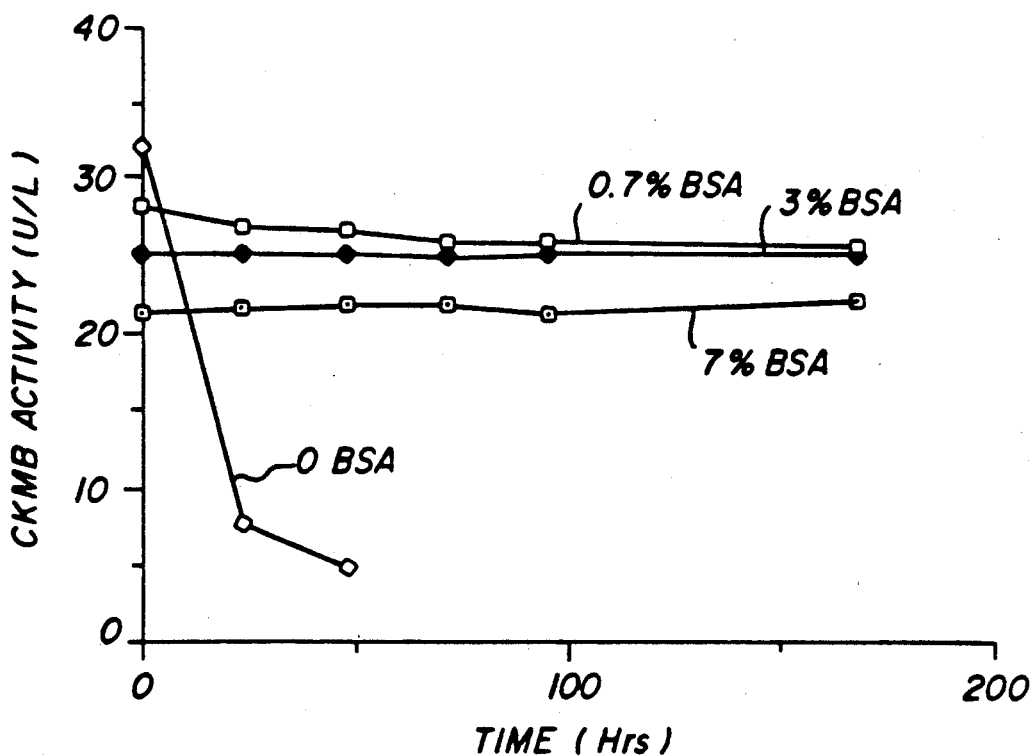
FIG. 2 is a graph showing CK-MB activity over time for various compositions having varying concentrations of sulfhydryl modified bovine serum albumin (BSA).

CK-MB compositions were prepared as in Example 1 with increasing concentrations of sulfhydryl modified BSA. A control which contains no protein was also prepared. Compositions were kept refrigerated between CK-MB activity determinations on the Kodak Ektachem TM 700 Analyzer. The results in FIG. 2 show that a protein solution is needed to stabilize the activity of CK-MB in the composition. Activity of CK-MB is rapidly lost if no protein is present in the solution. The preparation with 3 g/dL unreactive BSA appears to be most stable in enzyme activity.

EXAMPLE 2

Composition with total CK

Studies were conducted to determine the long term stability of total CK activity in compositions of the invention. Total CK comprises subunits or isoenzymes CK-MM, CK-MB, and CK-BB.

For this test, CK-MM was added to sample B, the composition defined above in the assays for CK-MB activity, to form Sample C. CK-MM for this test was obtained from Scripps, catalog #C1324, but other sources of CK-MM would also be useful. The initial CK activity of Sample C, as determined on the Kodak Ektachem TM autoanalyser using the Kodak Ektachem TM CK analytical element, was 100 U/L, representing about 25 U/L of CK-MB and the remaining CK activity as CK-MM.

Sample D represents a prior art CK composition prepared in a protein solution of reactive human serum 5.3 g/dL at pH 7.0 and includes: a reducing agent, B-thio-D-glucose (3 mM); CK-MB from human heart; and CK-MM as found in human serum. Both samples C and D were stored at room temperature, so as to exert thermal stressing, and tested for CK activity stability over a period of 7 days. This test was conducted as in Example 1 except that the duration of the testing period was different.

Figure 3:
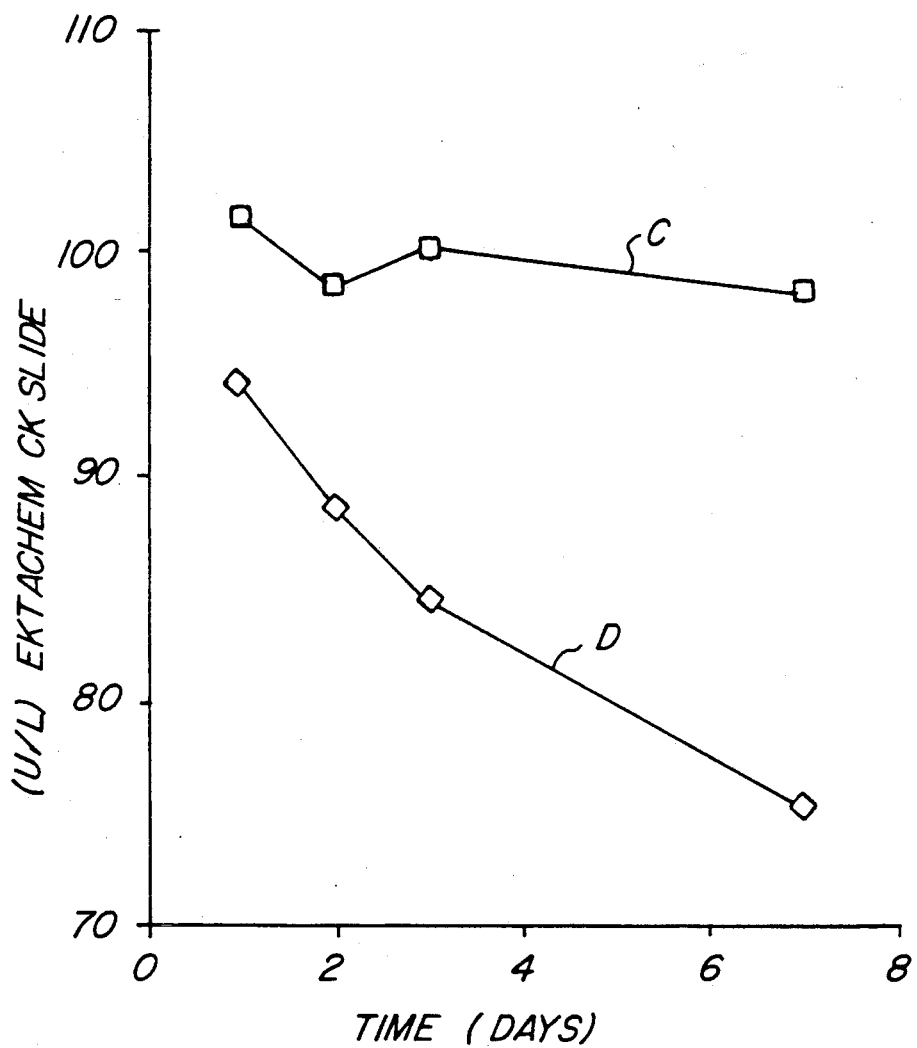
FIG. 3 is a graph showing the stability of total CK over time for a composition of the invention and for a prior art composition.

FIG. 3 shows the stability of total CK activity in the composition of the invention (Sample C) and in the prior art composition (Sample D). The graph of FIG. 3 shows that the CK composition of the invention showed little loss of CK activity after 7 days, while the prior art composition deteriorated steadily from the very first day. These results demonstrate that the method of the invention is applicable to CK-MB as well as to total CK.

The invention has been described in detail with particular reference to certain preferred embodiments thereof, but it will be understood that variations and modifications can be effected within the spirit and scope of the invention.

I claim:

1. A composition comprising (a) a protein selected from the group consisting of animal serum and albumin derived from serum, said protein also having sulfhydryl groups blocked with cystine and (b) creatine kinase, said composition being prepared by adding creatine kinase to the protein.

2. The composition of claim 1 wherein the the activity of creatine kinase is between about 1 and 2000 U/L.

3. The composition of claim 1 wherein the creatine kinase is the isoenzyme CK-MB.

4. The composition of claim 2 wherein the protein is bovine serum albumin.

5. The composition of claim 2, also comprising a metal chelator.

6. The composition of claim 2 also comprising magnesium.

7. The composition of claim 2, also comprising a buffer having a pH of about 8.5.

8. The composition of claim 2 in lyophilized form.

9. The composition of claim 8 wherein said composition is reconstituted from the lyophilized composition of claim 8.

10. An enzyme composition prepared by the steps of:
   (a) preparing a solution of protein in water wherein the protein has sulfhydryl groups blocked with cystine and is selected from the group consisting of animal serum and albumin derived from serum; and
   (b) adding creatine kinase to the solution of (a).

* * * * *